(12) United States Patent
Brehm et al.

(10) Patent No.: US 6,623,848 B2
(45) Date of Patent: Sep. 23, 2003

(54) WATER-ABSORBING POLYMERS HAVING INTERSTITIAL COMPOUNDS, A PROCESS FOR THEIR PRODUCTION, AND THEIR USE

(75) Inventors: Helmut Brehm, Krefeld (DE); Jorg Harren, Krefeld (DE); Jorg Issberner, Krefeld (DE); Richard Mertens, Krefeld (DE)

(73) Assignee: Stockhausen GmbH & Co. KG (DE)

( * ) Notice: Subject to any disclaimer, the term of this patent is extended or adjusted under 35 U.S.C. 154(b) by 0 days.

(21) Appl. No.: 10/076,768

(22) Filed: Feb. 14, 2002

(65) Prior Publication Data

US 2003/0157318 A1 Aug. 21, 2003

(51) Int. Cl.$^7$ .......................... A61F 13/15; B01J 29/06
(52) U.S. Cl. .................. 428/327; 162/175; 162/181.5; 162/181.6; 162/187; 162/231; 502/64; 502/70; 428/328; 428/329; 604/368; 604/376
(58) Field of Search .............. 162/175, 181.5, 162/181.6, 187, 231; 604/368, 376; 502/64, 70; 428/327, 328, 329

(56) References Cited

U.S. PATENT DOCUMENTS

| | | | |
|---|---|---|---|
| 3,453,257 A | 7/1969 | Parmerter et al. | |
| 3,740,391 A | 6/1973 | Williams et al. | |
| 4,076,663 A | 2/1978 | Masuda et al. | |
| 4,153,585 A | 5/1979 | Tessler | |
| 4,286,082 A | 8/1981 | Tsubakimoto et al. | |
| 4,638,058 A | 1/1987 | Brandt et al. | |
| 4,654,039 A | 3/1987 | Brandt et al. | |
| 4,666,983 A | 5/1987 | Tsubakimoto et al. | |
| 5,037,412 A | 8/1991 | Tanzer et al. | |
| 5,134,127 A | 7/1992 | Stella et al. | |
| 5,154,713 A | 10/1992 | Lind | |
| 5,306,487 A * | 4/1994 | Karapasha et al. | 424/76.6 |
| 5,314,420 A | 5/1994 | Smith et al. | |
| H1579 H * | 8/1996 | Furio | 604/359 |
| 5,691,421 A * | 11/1997 | Tanaka et al. | 525/329.2 |
| 5,714,445 A * | 2/1998 | Trinh et al. | 510/103 |
| 6,225,524 B1 * | 5/2001 | Guarracino et al. | 604/359 |
| 6,229,062 B1 * | 5/2001 | Mandell et al. | 604/367 |
| 6,245,693 B1 * | 6/2001 | Gagliardi et al. | 442/76 |
| 6,284,231 B1 * | 9/2001 | Trinh et al. | 424/76.1 |

FOREIGN PATENT DOCUMENTS

| | | |
|---|---|---|
| DE | 27 06 135 C2 | 2/1977 |
| DE | 35 03 458 C2 | 2/1985 |
| DE | 35 08 280 A1 | 3/1985 |
| DE | 35 44 770 C2 | 12/1985 |
| DE | 40 20 780 C1 | 6/1990 |
| DE | 42 26 739 A1 | 8/1992 |
| DE | 42 44 548 C2 | 12/1992 |
| DE | 43 33 056 C2 | 9/1993 |
| DE | 44 18 818 C2 | 5/1994 |
| DE | 195 20 989 A1 | 6/1995 |
| DE | 195 32 500 A1 | 9/1995 |
| DE | 196 09 947 A1 | 3/1996 |
| DE | 197 17 798 A1 | 4/1997 |
| EP | 0 389 023 A2 | 9/1990 |
| EP | 0 516 949 B1 | 4/1992 |
| EP | 0 509 409 A1 | 10/1992 |
| EP | 0 510 619 A1 | 10/1992 |
| EP | 0 339 461 B1 | 1/1993 |
| EP | 0 317 106 B1 | 2/1993 |
| EP | 0 806 194 A1 | 11/1997 |
| EP | 0 806 195 A1 | 11/1997 |
| EP | 0 811 387 A1 | 12/1997 |
| EP | 0 811 388 A1 | 12/1997 |
| EP | 0 811 389 A1 | 12/1997 |
| EP | 0 811 390 A1 | 12/1997 |
| EP | 0 850 617 A1 | 7/1998 |
| EP | 0 850 623 A1 | 7/1998 |
| FR | 2 755 612 A1 | 11/1996 |
| WO | WO 91/11977 | 8/1991 |
| WO | WO 91/12029 | 8/1991 |
| WO | WO 91/12031 | 8/1991 |
| WO | WO 94/09043 | 4/1994 |
| WO | WO 94/22500 | 10/1994 |
| WO | WO 94/22501 | 10/1994 |
| WO | WO 94/25077 | 11/1994 |
| WO | WO 97/01317 | 1/1997 |
| WO | WO 97/40802 | 11/1997 |
| WO | WO 97/46193 | 12/1997 |
| WO | WO 97/46195 | 12/1997 |
| WO | WO 97/49487 | 12/1997 |
| WO | WO 98/17239 | 4/1998 |
| WO | WO 98/17240 | 4/1998 |
| WO | WO 98/18439 | 5/1998 |

OTHER PUBLICATIONS

Christian Rousell and Anita Favrou, Journal of Chromatography A, 704 (1995) 67–74.

Alan P. Croft and Richard A. Bartsch, Tetrahedron, vol. 39, No. 9, pp. 1417–1473.

Nikolaos A. Peppas, Hydrogels in Medicine and Pharmacy vol. III (1987) pp. 1–16.

\* cited by examiner

*Primary Examiner*—H. Thi Le
(74) *Attorney, Agent, or Firm*—Smith Moore LLP

(57) ABSTRACT

The invention relates to absorvents for water and aqueous liquids, which are vased on water-swell-able, yet water-insoluble polymers wherein cyclodextrin or cyclodextrin derivatives and zeolites high in silicon have been incorporated ionically, covalently and/or as a result of mechanical inclusion.

9 Claims, No Drawings

WATER-ABSORBING POLYMERS HAVING INTERSTITIAL COMPOUNDS, A PROCESS FOR THEIR PRODUCTION, AND THEIR USE

The invention relates to absorbents for water and aqueous liquids, which absorbents are based on water-swellable, yet water-insoluble polymers wherein cyclodextrin or cyclodextrin derivatives and zeolites high in silicon have been incorporated ionically, covalently and/or as a result of mechanical inclusion.

Commercially available superabsorbing polymers essentially are crosslinked polyacrylic acids, crosslinked starch/acrylic acid graft copolymers, crosslinked hydrolyzed starch/acrylonitrile graft copolymers, crosslinked poly (maleic anhydride-co-isobutylene), or mixtures of various of the above-mentioned crosslinked polymers, wherein the carboxylic groups have been-subjected to partial neutralization with sodium and/or potassium ions. Such polymers find use e.g. in hygiene articles capable of absorbing body fluids such as urine or menstrual fluid or in absorbent pads in packagings for foodstuffs where they absorb large amounts of aqueous liquids and body fluids such as urine or blood with swelling and formation of hydrogels. Furthermore, the absorbed amount of liquid must be retained under a pressure typical of use. During the further technical development of superabsorbing polymers, the pattern of requirements to be met by these products has changed significantly over the years.

To date, the development of superabsorbers has been forced particularly with respect to the amount of absorbed liquid and pressure stability. Such crosslinked polymer products based on monomers containing acid groups are obtained by using one or more primary crosslinkers and/or one or more secondary crosslinkers and exhibit a combination of properties, namely, high retention, high absorption under pressure, low solubles, rapid absorption of liquid, and high permeability in the swollen state, which has not been achieved so far. When used in hygiene articles, these crosslinked polymer products have the advantage that secreted fluids, once absorbed by the polymer product, can no longer contact the skin. Thus, skin lesions such as diaper dermatitis can largely be avoided. Such comfort can even be increased by absorbing malodorous compounds.

According to Römpp Chemie Lexikon, the content of urine components and thus, of malodorous compounds, is subject to physiological fluctuations; also, particular substances are secreted at concentrations varying within a daily period, so that more precise data on the urine composition invariably are related to the so-called 24 hour urine which, in a healthy adult, contains e.g. urea average 20 g), uric acid (0.5 g), creatinine (1.2 g), ammonia (0.5 g), amino acids (2 g), proteins (60 mg), reducing substances (0.5 g, about 70 mg of which are D-glucose or urine sugar), citric acid (0.5 g) and other organic acids, as well as certain vitamins (C, $B_{12}$ etc.). The following inorganic ions are present: $Na^+$ (5.9 g), $K^+$ (2.7 g), $NH_4^+$ (0.8 g), $Ca^{2+}$ (0.5 g), $Mg^{2+}$ (0.4 g); $Cl^-$ (8.9 g), $PO_4^{3-}$ (4.1 g), $SO_4^{-2}$ (2.4 g). The dry content is between 50 and 72 g. Inter alia, alkylfurans, ketones, lactones, pyrrole, allyl isothiocyanate, and dimethyl sulfone have been recognized as volatile components of urine. Most of the volatile components are molecules having a molar mass below about 1000 g/mol and a high vapor pressure.

Volatile components of urine have also been investigated by, inter alia, A. Zlatkis et al. (Anal. Chem. Vol. 45, 763ff.). It is also well-known that consumption of asparagus results in an increase of the concentration of organic sulfur-containing compounds in human urine (R. H. Waring, Xenobiotika, Vol. 17, 1363ff.). In patients who are subject to specific diets and/or ingest specific medications, or in elderly individuals with decreasing kidney function, the urine may include malodorous substances. Patients suffering from urine incontinence have an increased secretion of ureases which convert the urea contained in urine, thereby liberating toxic ammonia. Also, a pathological change is well-known which is referred to as fish smell syndrome. It results from an increased secretion of quaternary ammonium compounds. Also, menstrual fluid may acquire an unpleasant odor. Among other things, this odor is produced by microbial degradation of secreted proteins. Typical odorous substances in menstrual fluid and the smells produced by degradation of blood components are not substantially different from the smell of components occurring in urine. In this case as well, low molecular weight compounds having a molar weight of less than 1000 g/mol are involved. Predominantly, nitrogen-containing heterocycles such as pyrrole, pyridine and derivatives thereof may be mentioned. Furthermore, those smells liberated by foodstuffs may be mentioned, e.g. the smell of fish (amines).

The odorous components in vaginal secretions and menstruation fluid have been investigated by G. Huggins and G. Preti (Clinical Obstetrics and Gynecology, Vol. 24, No. 2, June 1981, 355–377), where low molecular weight substances having a molar weight below 500 g/mol have been found. Fatty acids (e.g. butyric acid, isovaleric acid) and some aromatic compounds such as pyridine, indole and thymine may be emphasized, which particularly contribute to unpleasant odors. The amount of volatile fatty acids varies over the time period of the menstrual cycle (Human Vaginal Secretions: Volatile Fatty Acid Content, Richard P. Michael, R. W. Bonsall, Patricia Warner, Science, Dec. 27, 1974, 1217–1219). Amines have not been found in vaginal secretions and menstruation fluid. This is because the pH value of the secretion in a healthy female patient is in the acidic range where, at most, ammonium salts are present which are non-volatile. It is only in pathological conditions where proteins increasingly can be converted to amines by bacterial degradation, which may enter the vapor space in case of a simultaneous increase of the pH value.

Previous approaches of achieving an odor reduction in incontinence products and Ladies' hygiene products are based on reducing the concentration of free ammonia. Basically, there are two approaches to this end: preventing additional production of ammonia from urea degradation by suitable urease inhibitors (A. Norberg et al., Gerontology, 1984, 30, 261ff.), or by protonating free ammonia and binding thereof in the form of a carboxylate ammonium salt. This method is disadvantageous in that essentially, merely ammonia and other nitrogen-containing components can be controlled. Malodorous compounds lacking basic groups, e.g. thiols, are still capable of entering the vapor space.

It is well-known to those skilled in the art that certain interstitial molecules, also referred to as endohedral or concave molecules, are capable of incorporating other, mostly smaller, so-called guest molecules, thereby forming a host-guest complex. Such complex formation has an effect on the chemical and physical properties of both guest and host molecule. Cyclodextrins are formed during starch degradation by *Bacillus macerans* or *Bacillus circulans* under the action of cyclodextrin glycosyl transferase. They are comprised of 6, 7 or 8 glucose units α-1,4-linked to form a ring (α-, β- or γ-cyclodextrins). They are capable of entrapping hydrophobic guest molecules in varying amounts up to saturation ("molecular encapsulation"), e.g. gases, alcohols or hydrocarbons. The use of cyclodextrins as host molecule is reported comprehensively in the work of J. Szejtli (Cyclodextrin Technology, Kluwer Academic Publishers, 1988).

Polymers containing cyclodextrin are well-known. Thus, the patent application EP 483,380 A1 describes cyclodextrin-containing polymers where aldehyde groups in a protected or unprotected form are introduced into the cyclodextrin to react with nucleophilic groups of the polymer to form covalent bonds.

Crosslinked, water-swellable, hydrophilic cyclodextrin bead polymers are known from U.S. Pat. No. 5,360,899, which polymers are produced using hydroxyalkylcyclodextrins and epichlorohydrin or polyepoxide type crosslinkers with subsequent alkoxylation. These polymer-immobilized cyclodextrins have been suggested for use in chromatographic separation columns.

Crosslinked, water-swellable, hydrophilic cyclodextrin bead polymers are known from U.S. Pat. No. 5,357,012, which polymers are constituted of cyclodextrins bearing methacrylate groups and comonomers such as hydroxyethyl acrylate. Like-wise, these polymer-immobilized cyclodextrins have been suggested for use in chromatographic separation columns.

DE 195 20 989 A1 describes covalent binding of reactive cyclodextrin derivatives having at least one nitrogen-containing heterocycle to polymers bearing at least one nucleophilic group. Examples of nucleophilic groups are —OH, —NH, or —SH groups. Also, polymerizable cyclodextrin derivatives are mentioned which are copolymerized after suitable modification with other monomers, e.g. ethylenically unsaturated compounds.

For example, EP 806,195 A1 and WO 94/22500 teach the use of non-derivatized cyclodextrin as solid in hygiene products. Therein, coatings of powdered absorbents have also been described. However, one drawback is the lacking binding between cyclodextrin and the powdered absorbent, so that the cyclodextrin may be washed out during use, resulting in demixing during storage or transportation. Ultimately, these mixtures of absorbents and cyclodextrin lead to loss of effectiveness in odor absorption, because the absorbents absorbing the aqueous medium are largely separated from the cyclodextrin deodorant as a result of demixing processes.

To achieve improved adhesion of the cyclodextrin on powdered absorbents, WO 94/22501 teaches addition of polyethylene glycols or other linear polymers to cyclodextrin in a "melt" or in solution and subsequent spraying on the powdered absorbent. However, as is well-known to those skilled in the art, linear polymers preferably "thread" into the cyclodextrin cavity, which fact is advantageously utilized in supramolecular chemistry in order to produce e.g. rotaxans or catenanes (cf. the documents U.S. Pat. No. 5,538,655; G. Wenz, Angew. Chem. 1994, 106, 851). Therefore, the process described in WO 94/22501 is particularly disadvantageous, because the cyclodextrin interstices after such a polyethylene glycol pre-treatment are no longer quantitatively available for absorbing malodorous compounds.

With respect to odor control or reduction of malodorous compounds, no quantitative statements can be inferred from the above-mentioned documents, e.g. EP 806,195 A1, WO 94/22501, and WO 94/22500.

Zeolites mostly are synthetic compounds comprised of silicon oxide, aluminum oxide and a number of metal ions. Their composition is $M_2O_z.Al_2O_3.xSiO_2.yH_2O$ wherein M=uni- or multivalent metal, H, ammonium, etc., z=valency, x=from 1.8 to about 12, and y=from 0 to about 8. Structurally, zeolites are comprised of $SiO_4$ and $AlO_4$ tetrahedrons linked via oxygen bridges, thereby forming a channel system of equally structured and equally large interconnected cavities. When heated, most zeolites release their water continuously, without altering their crystal structure. In this way, they are capable of accommodating other compounds, acting as e.g. catalysts or ion exchangers. Furthermore, zeolites exhibit a screening effect by incorporating molecules having a smaller cross-section than the pore openings in the lattice channel system. Larger molecules are excluded. Cations are required to balance the negative charge of the $AlO_4$ tetrahedrons in the alumosilicate skeleton.

Inter alia, the synthesis of zeolites has been described extensively in: Zeolite Synthesis, ACS Symposium Series 398, Eds. M. L. Ocelli and H. E. Robson (1989) pp. 2–7. The synthesis of hydrophobic zeolites having a silicon dioxide/aluminum oxide ratio in the skeleton of >100, high hydrothermal stability and resistance to aqueous alkaline solutions is disclosed in the patent application DE 195 32 500 A1. The zeolites have a grain size of markedly less than 150 μm.

The patent document U.S. Pat. No. 4,795,482 teaches the use of hydrophobic zeolites to suppress and avoid organic odors. The reduction of odors was measured using head-space gas chromatography.

It is well-known from the patent applications WO 91/12029 and WO 91/12031 that the hydrophobic zeolites described in U.S. Pat. No. 4,795,482 or produced in a similar way can be used in combination with superabsorbers, where the zeolite is "essentially" bound to the superabsorber. The composites thus obtained are used in hygiene articles such as diapers or liners. The mixture is produced by mixing the superabsorber with the zeolite in dry condition. Water is subsequently added, where aggregation of the particles has been observed (WO 91/12031). Following a drying step, the mixture can be incorporated in hygiene products. In the patent application WO 91/12029, the zeolite is dispersed in water together with a binder and coated onto the superabsorber in a coating process where at least 20% zeolite, relative to the superabsorber, is to be used.

Both of these procedures are disadvantageous in that binding of the zeolite material to the polymer is exceedingly weak, and separation and demixing of superabsorber and zeolite may occur even at low mechanical stress on the composite. Such mechanical stress occurs e.g. when conveying a superabsorber and/or an absorbent article including superabsorbing polymers. In addition to demixing, problems of handling exceedingly fine particles also arise. Also, when subjecting the superabsorber to a secondary treatment with aqueous dispersions possibly containing binders, damage to the superabsorber structure and the associated swelling properties must be expected. The high percentage of non-swellable zeolite material in the superabsorber composite represents an additional limitation to the pattern of properties.

It is well-known from the patent applications EP 0,811, 387 A1 and EP 0,811,390 A1 that zeolites having a silicon dioxide/aluminum oxide ratio of from 1 to 5 can be used as odor absorbents in liners. The products produced according to the above document were subjected to a practical test, and the used products were rated in an olfactory test panel with test persons. The dry mixtures described in the above-mentioned patent applications readily undergo demixing. In addition, the amounts of required zeolite as taught in the above patent applications are exceedingly high, having a disadvantageous effect on the wearing comfort of hygiene articles.

The present invention therefore is based on the object of providing a polymer capable of absorbing water and aqueous liquids, which polymer has a substance by means of which malodorous organic compounds such as occurring e.g. in urine or other fluids secreted from the body are bound, and wherein malodorous materials released into the vapor space during use are markedly reduced;

a virtually uniform distribution of deodorant substance in the absorbent is present;

demixing in the condition prior to and during use is avoided as much as possible;

the absorbent has good retention properties and swelling properties under pressure; and the deodorant modification is ensured using amounts of deodorant substance as low as possible.

The present invention is also based on the object of providing a process for producing said absorbent polymer, wherein in particular, problems with mixing of dry substances differing substantially in their particle size, such as granulates and powders, are avoided;

no dust is formed; and aggregation of the particles during production is avoided.

According to the invention, said object is accomplished by means of an absorbent polymer constituted of crosslinked, monoethylenically unsaturated, partially neutralized monomers bearing acid groups, which polymer has $\alpha,\beta,\gamma,\delta$-cyclodextrins or derivatives thereof alone or in mixtures, as well as zeolites high in silicon bound or incorporated in an ionical, covalent or mechanical fashion.

In the meaning of the invention, "high in silicon" means that the silicon dioxide/aluminum oxide ratio is >10, preferably >20, more preferably >50, and even more preferably >100. A silicon dioxide/aluminum oxide ratio of >500 is particularly preferred.

In the meaning of the invention, "crosslinked" means that the polymer is crosslinked and/or surface-crosslinked.

According to the invention, the absorbent polymer includes $\alpha,\beta,\gamma,\delta$ type cyclodextrins and derivatives thereof.

The basic body of a chemically non-modified cyclodextrin has the following structure:

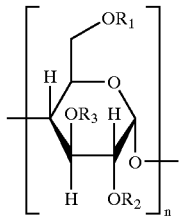

The anhydroglucose units are linked in a cyclic fashion to form rings, with $R_1=R_2=R_3=H$ ($\alpha$-cyclodextrin: n=6, $\beta$-cyclodextrin: n=7, $\gamma$-cyclodextrin: n=8). For example, non-modified cyclodextrins are commercially available under the designation of Cavitron by the company Cerestar, or Kleptose by the company Roquette, or by the company Wacker.

In cyclodextrin derivatives, n different substituents per residue ($R_1$–$R_3$) are possible which may be the same or independently different in chemical terms.

Above all, those cyclodextrin derivatives are possible which permit an ionical or covalent type chemical linkage to the absorbents bearing acid groups. Covalent linkages preferably are produced via formation of C—C bonds. For example, this type includes cyclodextrin derivatives containing ethylenically unsaturated groups incorporated covalently in the polymer chain already during polymerization of the absorber. For example, such groups are the (meth)acrylic, (meth)allyl and vinyl groups. According to the invention, however, covalent linkage of the cyclodextrins to the polymer skeleton, particularly in the form of ether, amide or ester groups, is also possible subsequent to polymerization.

Ionic binding of the cyclodextrin derivatives is effected using anionic or cationic groups, with cationic groups being preferred. Frequently, it is advantageous when the cyclodextrin molecules have multiple substitutions with ionic groups. Examples of anionic groups are the carboxylate, sulfate and sulfonate groups. Examples of cationic groups are quaternized nitrogens.

Ionic cyclodextrins can be obtained by reacting cyclodextrin derivatives with reactive compounds such as chloroacetic acid, sodium chloroacetate, maleic acid, maleic anhydride, and succinic anhydride. In an aqueous solution, these reaction products, e.g. carboxymethylcyclodextrin, carry a negative charge in a basic medium due to the carboxylate group.

Cyclodextrin derivatives to be used according to the invention and having at least one nitrogen-containing heterocycle can be produced e.g. according to the process described in DE 195 20 989 A1. This patent application is hereby incorporated by reference and thus represents part of the disclosure. In this way, cyclodextrin derivatives can be obtained, which include another group active towards nucleophilic groups. These derivatives can undergo direct reaction with polymers bearing nucleophilic groups. Examples of nucleophilic groups are —OH, —NH or —SH groups.

Other chemically modified cyclodextrins to be used according to the invention can be obtained using the process described in A. P. Croft and R. A. Bartsch, Tetrahedron Vol. 39, No. 9, pp. 1417–1473. They are obtained by reacting nitrogen-containing compounds wherein one or more functional groups are capable of reacting with hydroxyl groups of the cyclodextrins to form e.g. ethers, esters, acetals. The above citation is hereby incorporated by reference and thus represents part of the disclosure.

Cationic cyclodextrins such as described in Ch. Roussel, A. Favrou, Journal of Chromatography A, 704 (1995), 67–74, are particularly preferred. They can be produced by reacting cyclodextrin with e.g. N-(3-chloro-2-hydroxypropyl)-N,N,N-trimethylammonium chloride. The above citation is here-by incorporated by reference and thus represents part of the disclosure. The ionic cyclodextrins including at least one nitrogen-containing aliphatic residue, which can be used according to the invention, may also be produced according to the procedures described in U.S. Pat. Nos. 3,740,391; 4,153,585 and 4,638,058, for example. These patents are hereby incorporated by reference and thus representpart of the disclosure: For example, N,N-dimethylaminoethyl (meth)acrylate, N,N-dimethylaminopropyl (meth)acrylate, N,N-dimethylaminoethyl (meth) acrylamide, and N,N-dimethylaminopropyl(meth) acrylamide may be mentioned as suitable monomers. Preferably, N,N-dimethyl-aminoethyl acrylate and N,N-dimethylaminopropylacrylamide are employed.

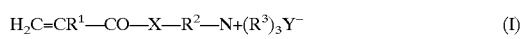

wherein $R^1$=H, $CH_3$, $R^2$=$C_2$–$C_4$ alkylene group, $R^3$=H, $C_1$–$C_4$ alkyl group,

X=O, NH,

Y=cl, $SO_4$.

The average degree of substitution (DS value) per anhydroglucose for substituents containing nitrogen can be determined according to methods known from literature using elemental analysis as described e.g. in U.S. Pat. No. 5,134,127 and U.S. Pat. No. 3,453,257 for substituents containing sulfur or nitrogen. When using the synthetic methods described in U.S. Pat. Nos. 3,740,391 and 4,153,585, the DS value can be varied within wide limits. These patents are hereby incorporated by reference and thus represent part of the disclosure.

3 hydroxyl groups per anhydroglucose unit of a cyclodextrin are capable of undergoing further reaction. Therefore, the degree of substitution e.g. in case of β-cyclodextrin can be between 0.05 and 3 at maximum. A degree of substitution below 0.05 indicates that a mixture of non-modified cyclodextrin and chemically modified cyclodextrin is present.

In order to modify the properties, it is also possible to employ cyclodextrins which, in addition to the above-mentioned groups required for binding to the absorber, contain further substituents having no reactivity towards the polymer. For example, these include reaction products of cyclodextrins with alkylating agents, e.g. $C_1$–$C_{22}$ alkyl halides, e.g. methyl chloride, ethyl chloride, butyl chloride, butyl bromide, benzyl chloride, lauryl chloride, stearyl chloride, or dimethyl sulfate, or reaction products of cyclodextrins with alkylene oxides such as ethylene oxide, propylene oxide, butylene oxide, or styrene oxide.

The amount of cyclodextrin or derivative thereof to be employed according to the invention is 0.01–50 wt.-%, preferably 0.1–30 wt.-%, more preferably 0.5–10 wt.-%, relative to the total amount of powdered absorbent.

The zeolites to be used according to the invention are dealuminized, hydrophobic (organophilic) zeolite variants having a silicon dioxide/aluminum oxide ratio in their skeletons of >10, preferably >20, more preferably >50, with >100 being particularly preferred. A silicon dioxide/aluminum oxide ratio of >500 is most preferred. The amount to be used is 0.01–10 wt.-%, preferably 0.1–5 wt.-%, and more preferably 0.70–3 wt.-%, relative to the total amount of polymer product. For example, such zeolites are traded by Degussa AG under the trade name Flavith® or by UOP under the designation of Abscents®. Flavith® is characterized in more detail in the KC-CZ 42-1-05-1098 T&D product data sheet. Said product data sheet is hereby incorporated by reference and thus represents part of the disclosure.

Various processes are possible for polymerizing the polymer of the invention optionally having superabsorbent properties, e.g. bulk polymerization, solution polymerization, spray polymerization, inverse emulsion polymerization, and inverse suspension polymerization. Preferably, a solution polymerization is performed using water as solvent. The solution polymerization may be conducted in a continuous or batchwise fashion. The patent literature includes a broad spectrum of possible variations with respect to concentration conditions, temperatures, type and amount of initiators and of secondary catalysts. Typical processes have been described in the following patent specifications: U.S. Pat. No. 4,286,082; DE 27 06 135, U.S. Pat. No. 4,076,663, DE 35 03 458, DE 40 20 780, DE 42 44 548, DE 43 23 001, DE 43 33 056, DE 44 18 818. These disclosures are hereby incorporated by reference and thus represent part of the disclosure.

The unsaturated acid group-containing monomers to be used according to the invention are, e.g. acrylic acid, methacrylic acid, crotonic acid, isocrotonic acid, maleic acid, fumaric acid, itaconic acid, vinylacetic acid, vinylsulfonic acid, methallylsulfonic acid, 2-acrylamido-2-methyl-1-propanesulfonic acid, as well as the alkali and/or ammonium salts thereof. It is preferred to use acrylic acid and its alkali and/or ammonium salts and mixtures thereof. Furthermore, it is also possible to use monomers being hydrolyzed to form acid groups as late as subsequent to the polymerization as is possible e.g. with nitrile groups.

In order to modify the polymer properties, up to 30 wt.-% of other comonomers soluble in the aqueous polymerization batch, such as acrylamide, methacrylamide, acrylonitrile, (meth)allyl alcohol ethoxylates, and mono(meth)acrylic acid esters of alcohols or ethoxylates can optionally be used.

Minor amounts of crosslinking monomers having more than one reactive group in their molecules are copolymerized together with the above-mentioned monomers, thereby forming partially crosslinked polymer products which are no longer soluble in water but merely swellable. Bi- or multifunctional monomers, e.g. amides such as methylenebisacryl- or -methacrylamide, or ethylenebisacrylamide may be mentioned as crosslinking monomers, and also, allyl compounds such as allyl (meth)acrylate, alkoxylated allyl (meth)acrylate reacted preferably with from 1 to 30 mol of ethylene oxide, triallyl cyanurate, maleic acid diallyl ester, polyallyl esters, tetraallyloxyethane, triallylamine, tetraallylethylenediamine, allyl esters of phosphoric acid or phosphorous acid, and also, crosslinkable monomers such as N-methylol compounds of unsaturated amides like methacrylamide or acrylamide and the ethers derived therefrom, as well as esters of polyols and alkoxylated polyols, such as diacrylates or triacrylates, e.g. butanediol or ethylene glycol diacrylate, polyglycol di(meth) acrylates, trimethylolpropane triacrylate, di- and triacrylate esters of trimethylolpropane preferably oxyalkylated (ethoxylated) with 1 to 30 mol alkylene oxide, acrylate and methacrylate esters of glycerol and pentaerythritol, and of glycerol and pentaerythritol preferably oxyethylated with 1 to 30 mol ethylene oxide. It is preferred to use triallylamine, acrylates of polyhydric alcohols or alkoxylates thereof, and methallyl alcohol acrylates or alkoxylates thereof. The ratio of crosslinking monomers is from 0.01 to 3.0 wt.-%, preferably from 0.05 to 2.0 wt.-%, and more preferably from 0.05 to 1.5 wt.-%, relative to the total monomers.

The acidic monomers preferably are subjected to neutralization. The neutralization can be performed in various ways. On the one hand, according to the teaching of U.S. Pat. No. 4,654,039, the polymerization may be conducted directly with the acidic monomers, with neutralization being effected subsequently in the polymer gel. This patent specification is hereby incorporated by reference and thus represents part of the disclosure. On the other hand and preferably, the acidic monomer components are neutralized to 20–95%, preferably 50–80% prior to polymerization, in which case they are present as sodium and/or potassium and/or ammonium salts at the time polymerization is begun. It is preferred to use those bases for neutralization which do not adversely affect the subsequent polymerization. It is preferred to use sodium or potassium hydroxide solution and/or ammonia, with sodium hydroxide solution being particularly preferred; addition of sodium carbonate, potassium carbonate or sodium bicarbonate may have an additional positive effect as taught in U.S. Pat. No. 5,314,420 and U.S. Pat. No. 5,154,713. Before initiating the polymerization in this adiabatic solution polymerization, the partially neutralized monomer solution is cooled to a temperature of below 30° C., preferably below 20° C. These patent specifications are hereby incorporated by reference and thus represent part of the disclosure. In the other processes mentioned, other temperatures are also well-known and conventional according to the state of the art.

The polymer products of the invention may contain water-soluble polymers as a basis for grafting in amounts up to 40 wt.-%. Inter alia, these include partially or completely saponified polyvinyl alcohols, starch or starch derivatives, cellulose or cellulose derivatives, polyacrylic acids, polyglycols, or mixtures thereof. The molecular weights of the polymers added as basis for grafting must be adapted to the circumstances of the polymerization conditions. In the event of an aqueous solution polymerization, for example, it may be necessary for viscosity reasons to employ low or medium molecular weight polymers only, whereas this factor plays a minor role in a suspension polymerization.

In addition to polymers obtained by crosslinking polymerization of partially neutralized acrylic acid, those are preferably used which additionally contain components of graft-polymerized starch, or of polyvinyl alcohol.

The polymerization process of the invention can be initiated by various conditions, e.g. by irradiating with radioactive, electromagnetic or ultraviolet radiation, or by a redox reaction of two compounds, e.g. sodium hydrogen sulfite with potassium persulfate, or ascorbic acid with hydrogen peroxide. The thermally induced decomposition of a socalled free-radical initiator such as azobisisobutyronitrile, sodium peroxodisulfate, t-butyl hydroperoxide, or dibenzoyl peroxide may also be used as initiation of polymerization. Furthermore, a combination of some of the above-mentioned methods is possible.

In principle, the polymer products are produced according to two methods:

According to the first method, the partially neutralized acrylic acid is converted to a gel by means of free-radical polymerization in aqueous solution and in the presence of crosslinkers and optional polymer additives, which gel is subsequently crushed and dried until a powdered, flowable state is reached, milled, and screened to the desired particle size. The solution polymerization may be conducted in a continuous or batchwise fashion. The patent literature includes a broad spectrum of possible variations with respect to concentration conditions, temperatures, type and amount of initiators, as well as a variety of secondary crosslinking options. Typical processes have been described in the following patent specifications: U.S. Pat. No. 4,076,663; U.S. Pat. No. 4,286,082; DE 27 06 135, DE 35 03 458, DE 35 44 770, DE 40 20 780, DE 42 44 548, DE 43 23 001, DE 43 33 056, DE 44 18 818. These documents are hereby incorporated by reference and thus represent part of the disclosure.

The inverse suspension and emulsion polymerization process may also be used to produce the polymer products. In these processes, an aqueous, partially neutralized solution of acrylic acid is dispersed in a hydrophobic organic solvent using protective colloids and/or emulsifiers, and the polymerization is initiated using free-radical initiators. The crosslinkers are either dissolved in the monomer solution and metered together with same or added separately and optionally subsequently. The optionally present polymeric grafting bases are added via the monomer solution or by directly placing in the oil phase. Subsequently, the water is removed azeotropically from the mixture, and the polymer product is filtrated and optionally crushed and dried until a powdered, flowable state is reached, milled, and screened to the desired particle size.

Using the process of subsequent surface crosslinking, the polymer products according to the invention can be improved in their pattern of properties, particularly in their absorption of liquid under pressure, so that the well-known phenomenon of "gel blocking" is suppressed, where slightly swelled polymer particles adhere to each other, thereby impeding further absorption of liquid and distribution of liquid e.g. within the diaper. In this secondary crosslinking, the carboxyl groups of the polymer molecules are crosslinked at the surface of the superabsorber particles at elevated temperature using crosslinking agents. Methods of secondary crosslinking have been described in several written specifications, e.g. in DE 40 20 780, EP 317,106 and WO 94/9043.

According to the invention, all those secondary crosslinking agents known to a person skilled in the art from U.S. Pat. No. 5,314,420, page 8, lines 3–45, may be used advantageously in combination with a primary crosslinker or a combination of crosslinkers. The above-mentioned documents are hereby incorporated by reference and thus represent part of the disclosure. As a rule, these compounds contain at least two functional groups capable of reacting with carboxylic acid or carboxyl groups. Alcohol, amine, aldehyde, and carbonate groups are preferred and also, crosslinker molecules having multiple different functions are employed. Preferably, polyols, polyamines, polyaminoalcohols, polyepoxides, and alkylene carbonates are used. In particular, one of the following secondary crosslinking agents is used: ethylene glycol, di-ethylene glycol, triethylene glycol, polyethylene glycol, glycerol, polyglycerol, propylene glycol, diethanolamine, triethanolamine, polypropylene glycol, block copolymers of ethylene oxide and propylene oxide, sorbitan fatty acid esters, ethoxylated sorbitan fatty acid esters, trimethylolpropane, ethoxylated trimethylolpropane, pentaerythritol, ethoxylated pentaerythritol, polyvinyl alcohol, sorbitol, ethylene carbonate, propylene carbonate. It is particularly preferred to use polyols and ethylene carbonate as secondary crosslinking agents. The secondary crosslinking agent is employed in an amount of from 0.01 to 30 wt.-%, preferably 0.1–10 wt.-%, relative to the polymer to be subjected to secondary crosslinking.

Prior to secondary crosslinking, the polymer preferably is dried, milled, screened for the respective grain fraction favorable in application-technical terms, and subsequently fed into the secondary crosslinking reaction. In some cases, however, it has proven beneficial to add the secondary crosslinkers at an early stage prior to drying the polymer gel or prior to crushing the partially or predominantly dried polymer. Secondary crosslinking to be performed according to the invention has been described in U.S. Pat. No. 4,666,983 and DE 40 20 780. These documents are hereby incorporated by reference and thus represent part of the disclosure. Advantageously, the secondary crosslinker frequently is added in the form of a solution in water, organic solvents or mixtures thereof, particularly in those cases where low amounts of secondary crosslinking agent are used. Suitable mixing apparatus for applying the secondary crosslinking agent are, e.g., Patterson-Kelley mixers, DRAIS turbulence mixers, Lödige mixers, Ruberg mixers, screw mixers, pan mixers, and fluid-bed mixers, as well as continuously operated vertical mixers wherein the powder is mixed at a rapid frequency using rotating knives (Schugi mixer). Once the secondary crosslinker has been mixed with the pre-crosslinked polymer, heating to temperatures of from 60 to 250° C., preferably from 135 to 200° C., and more preferably from 150 to 185° C. is effected in order to perform the secondary crosslinking reaction. The time period for additional heating is limited by that point where the desired pattern of properties of the polymer product is destroyed as a result of heat damage.

Depending on the type of use, various screening fractions are employed for processing the polymer products, e.g.

between −100 and 1000 μm and preferably between 150 and 850 μm for diapers. In general, this grain fraction is produced by milling and screening prior to and/or subsequent to secondary crosslinking.

In the polymer product of the invention for absorbing water or aqueous liquids, the cyclodextrin component and/or the zeolite component can be extracted by the liquid to be absorbed to only a lesser extent, or, in the dry state, undergo demixing to only a lesser extent. Surprisingly, it has been found that the cyclodextrins and zeolites not even partly lose their ability of absorbing odors as a result of the intimate linkage with the crosslinked polymer bearing acid groups, but rather, odor absorption compared to unbound cyclodextrin is even enhanced. In this way, the vapor space concentration of malodorous substances is effectively reduced. The deodorant substances are applied from an aqueous solution or suspension, for example. In this way, any dust problems during manufacturing are avoided. It has also been found that neither the zeolites lose their ability of absorbing odors when applied from an aqueous suspension. Furthermore, it has been found that the other quality criteria relevant for superabsorbers, namely, high retention and absorption against pressure, are not adversely affected by applying the deodorant substances cyclodextrin and zeolite.

As a result of embedding the cyclodextrins and zeolites in the polymer, strong binding between the cyclodextrin or the zeolite and the polymer is generated The polymer product of the invention is excellently suited for incorporating active substances, and when used, these active substances can optionally be released in a controlled fashion. By incorporation in the absorbents of the invention, the stability of sensitive active substances is markedly improved.

The present invention is also directed to a process for producing the absorbent polymer products of the invention.

According to the process of the invention, the absorbent polymer product of the invention is produced by:
free-radical polymerization of an aqueous solution of ethylenically unsaturated, optionally partially neutralized monomers bearing acid groups and crosslinking monomers according to the process of solution or suspension polymerization to form a hydrogel;
optional isolation;
crushing, followed by drying, milling;
optional screening; and
surface crosslinking;
wherein the cyclodextrin component and the zeolite high in silicon are added to the polymer product during its surface crosslinking at the latest.

Preferably, the cyclodextrin component and the zeolite high in silicon are added in solution or in suspension.

In the meaning of the invention, "high in silicon" means that the silicon dioxide/aluminum oxide ratio is >10, preferably >20, more preferably >50, and even more preferably >100. A silicon dioxide/aluminum oxide ratio of >500 is particularly preferred.

The cyclodextrin or its derivative and the zeolite are employed as a solution or suspension in a solvent. A preferred solvent is water, but mixtures of water and organic solvents are also used.

According to the invention, the addition of cyclodextrin and/or zeolite can be effected at various process stages in the production of the powdered polymer product, as illustrated below. By applying the cyclodextran orzeolite from an aqueous solution and/or suspension onto the polymer product prior to or during one of the process steps in the production thereof, particularly effective binding between the odor-absorbing component and the polymer product is achieved. Preferably, the solution is adjusted to a pH value of >8, preferably >9, more preferably >11, using potassium hydroxides or sodium hydroxide. It is also preferred that the temperature of the solution be 20–50° C.

In a preferred embodiment of the process according to the invention, the cyclodextrin or its derivative and the zeolite are added directly to the aqueous monomer solution prior to polymerization. In case the absorbent is produced by suspension polymerization, it is also possible to precharge all or part of the cyclodextrin and zeolite in the oil phase and meter the monomer solution thereto. Where only a part of the cyclodextrin and/or zeolite is precharged, the remainder is to be metered e.g. via the monomer solution.

In another preferred embodiment of the process according to the invention, cyclodextrin or its derivative and the zeolite are applied onto the crushed polymer gel in the form of a solution or suspension in water or an organic solvent or mixtures thereof.

Furthermore, the polymer gel preferably is subjected to at least partial drying and the cyclodextrin or its derivative and the zeolite subsequently are applied onto the powder in the form of a solution or suspension in water or an organic solvent or mixtures thereof. The resulting product can be dried directly as such and subjected to surface cross-linking.

In another preferred embodiment of the process according-to the invention, the cyclodextrin or its derivative and the zeolite are employed in the processing step of secondary crosslinking. Suitable mixing apparatus for applying the secondary crosslinking agent are e.g. Patterson-Kelley mixers, DRAIS turbulence mixers, Lodige mixers, Ruberg mixers, screw mixers, pan mixers, and fluid-bed mixers, as well as continuously operated vertical mixers wherein the powder is mixed at a rapid frequency using rotating knives (Schugi mixer).

It is also preferred to incorporate the cyclodextrins or their derivatives and/or the zeolites at various stages of the production process of the absorbent polymers so as to optimize the effect of the cyclodextrins and zeolites and utilize synergies. In this way it is possible, for example, to incorporate a non-modified cyclodextrin in the polymer particles via the monomer solution and fix an ionically modified cyclodextrin on the surface of the absorber during secondary surface crosslinking. Furthermore, it is also possible to add the cyclodextrins or their derivatives in one particular step of production and the zeolites in another.

According to another process of the invention, the absorbent polymer product of the invention is produced by:
free-radical polymerization of an aqueous solution of ethylenically unsaturated, optionally partially neutralized monomers bearing acid groups and crosslinking monomers according to the process of solution or suspension polymerization to form a hydrogel;
optional isolation;
crushing, followed by drying, milling;
optional screening;
wherein the cyclodextrin and the zeolite high in silicon are added to the polymer product at a stage where the water content thereof is at least 10 wt.-%.

Preferably, the addition of cyclodextrin component and zeolite high in silicon is effected in solution or in suspension.

According to the invention, the water content must not be reduced below 10 wt.-% before the cyclodextrin and zeolite high in silicon are added.

Preferably, the water content must not be reduced below 30 wt.-%, more preferably not below 50 wt.-%, and even more preferably not below 65 wt.-% before the cyclodextrin and zeolite high in silicon are added.

The addition of the cyclodextrin and/or zeolite to the polymer product preferably is effected using an aqueous solution and/or suspension. Preferably, the solution is adjusted to a pH value of >8, preferably >9, more preferably >11, using potassium hydroxide or sodium hydroxide. It is also preferred that the temperature of the solution be 20–50° C.

Using the process according to the invention, absorbent polymers are obtained wherein the cyclodextrin or its derivative and the zeolite are incorporated in the synthetic polymer in such a way that the amount of cyclodextrin extractable with water is significantly less than the amount actually contained in the final product. The extractable percentage of cyclodextrins is below 85% of the amount theoretically present in the product and generally is between 45 and 60%. Even after mechanical stressing, e.g. in a ball mill at 95 rpm for 6 minutes, the zeolite cannot be removed completely from the polymer product in the products produced according to the process of the invention, less than 80% and generally 40–60% of the total amount of zeolite applied onto the polymer product is removed after such stressing.

Compared to powdered absorbents including no cyclodextrin- or derivative thereof and no zeolite, the polymer products of the invention exhibit improved absorption of malodorous compounds.

The polymer products find use e.g. in hygiene articles capable of absorbing body fluids such as urine, or in the packaging sector, e.g. meat and fish products, where they absorb large amounts of aqueous liquids and body fluids such as urine, blood, or meat juice, with swelling and formation of hydrogels. Therefore, the present invention is also directed to these uses.

The polymer products of the invention are incorporated directly as powders in constructions for absorbing liquids, or previously fixed in foamed or non-foamed sheet materials. For example, such constructions for absorbing liquids are diapers for babies, incontinence articles or absorbent inserts in packaging units for foodstuffs. In the absorbent polymer product according to the invention, binding of the cyclodextrin or its derivative and of the zeolite to the polymer obviously is so strong that even under mechanical stress, e.g. when conveying the absorbent polymer product, substantial separation and demixing of the polymer and zeolite cannot be observed and thus, in particular, problems of handling exceedingly fine particles do not occur.

Further processing of the polymer product according to the invention is advantageous because, according to prior art, separate and uniform dosage of superabsorber and zeolite, particularly with small amounts of zeolite, cannot be achieved. The polymer product according to the invention, which allows easy dosing, ensures a constant concentration of polymer product with superabsorbent properties and deodorant component in absorbent articles such as liners.

Moreover, the absorbents of the invention were found to be excellently suited for incorporating active substances. The stability of sensitive active substances, e.g. with respect to oxidative degradation, is substantially improved as a result of incorporation in the absorbents of the invention.

Furthermore, the polymer products according to the invention find use in plant breeding and in pest control in agriculture. In plant breeding, the polymer products in the vicinity of plant roots provide for sufficient supply of liquid and previously incorporated nutrients and are capable of storing and releasing same over a prolonged period of time.

In pest control, the polymer product can incorporate single active substances or a combination of multiple active substances which in use are released in a controlled fashion in terms of time and amount.

The invention will be illustrated in the following Examples. These illustrations merely are given by way of example and do not limit the general idea of the invention.

Production and properties of the polymer products according to the invention will be explained. Furthermore, the test methods and procedures used to determine the characteristics of the polymers with superabsorbent properties will be described.

Test Methods

Test Method 1

The retention is determined according to the tea bag method and is given as mean value of three measurements. About 200 mg of polymer product is welded in a tea bag and immersed in a 0.9% NaCl solution for 30 minutes. The tea bag is subsequently centrifuged in a centrifuge (23 cm in diameter, 1400 rpm) for 3 minutes and weighed. A tea bag having no water-absorbing polymer is run as a blank.

$$\text{Retention} = \frac{\text{Final weight} - \text{Blank}}{\text{Initial weight}} \; [g/g]$$

Test Method 2: Liquid Absorption Under Pressure (AAP Test, EP 0,339,461)

The absorption under pressure (pressure load 50 g/cm$^2$) is determined according to the method described in EP 0,339,461, page 7. This document is hereby in corporated by reference and thus represents part of the disclosure. About 0.9 g of superabsorber is weighed in a cylinder having a screen bottom. The uniformly spread superabsorber layer is loaded with a piston exerting a pressure of 50 g/cm$^2$. The previously weighed cylinder then is placed on a glass filter plate situated in a tray containing a 0.9% NaCl solution, the liquid level of which precisely corresponds to the height of the filter plate. After allowing the cylinder unit to absorb 0.9% NaCl solution for 1 hour, it is reweighed, and the AAP is calculated as follows:

AAP=Final weight (cylinder unit+superabsorber)−Initial weight (cylinder unit+soaked superabsorber)/Initial weight of superabsorber Test Method 3

180 ml of an aqueous solution of sodium chloride is poured over 1 g of powdered absorbent, and this is stirred thoroughly for 1 hour (alternatively 16 hours) at room temperature. This is subsequently filtrated through a screen, and the concentration of cyclodextrin is determined according to the method below. This method is based on the reduction of light absorption (550 nm) of an alkaline solution of phenolphthalein in the presence of cyclodextrin which, as described by T. Takeuchi and T. Miwa, Chromatographia 1994, 38, 453, can be determined. The concentration obtained experimentally is divided by the concentration calculated theoretically. The theoretical concentration can be determined from the amount of cyclodextrin employed in the powder by dividing by 180. In this way, the extracted amount of cyclodextrin is obtained.

$$EA(CD) \% = \frac{\text{Concentration (CD) found} \times 100}{\text{Theoretical concentration (CD)}}$$

EA(CD): extractable percentage of cyclodextrin.

Test Method 4: Determination of the Absorption of Malodorous Compounds 0.1 g of powdered absorbent is added with 2 ml of an aqueous solution (including 5 wt.-% ethanol) of malodorous compound, and this is sealed in a 5 ml test vessel. This is allowed to stand at 23° C. for 12 hours, and the content of malodorous compound in the vapor space above the liquid is determined quantitatively against a blank using headspace GC.

Test Method 5

The silicon content of the absorbent polymers is determined by reacting silicate to form molybdenum blue and subsequent photometric analysis. Previously, the silicon has been reacted quantitatively to form silicate, using alkaline decomposition (Photometrische Analyse, Authors: B. Lange, Zdenek, J. Vejdelek, S., edition of 1987, p. 383, VCH).

EXAMPLES

Comparative Example 1, According to Patent Applications WO 94/22500 and WO 94/22501

9.850 g of a commercially available absorbent (Favor®, company Stockhausen GmbH) is mixed thoroughly with 0.15 g of solid β-cyclodextrin (beta-W7-cyclodextrin, technical grade, by Wacker company). Thereafter, the extractable amount of cyclodextrin is determined according to test method 1.

EA(CD)=93%

No cyclodextrin is detected in a blank with no cyclodextrin.

Comparative Example 2, According to Patent Applications WO 94/22500 and WO 94/22501

40 g of polyethylene glycol (m.w. 3000) is melted at elevated temperature. 40 g of cyclodextrin is added thereto, and the mixture is homogenized. A clear solution is formed after a short time. 9.40 g of a commercially available powdered absorbent (Favor®, company Stockhausen GmbH) is sprayed with 0.6 g of the cyclodextrin/polyethylene glycol solution, mixed thoroughly and cooled to room temperature. Thereafter, the extractable amount of cyclodextrin is determined according to test method 1.

EA(CD)=89%

Example 1a

This Example illustrates the production of a polymer gel having superabsorbent properties.

A solution of 1300 g of acrylic acid, 2115.9 g of distilled water, 2.7 g of polyethylene glycol monoallyl ether acrylate, and 1.25 g of polyethylene glycol diacrylate is prepared. Using 899.10 g of 50% sodium hydroxide solution, partial neutralization (degree of neutralization (DN): 60%) is effected with stirring and cooling. The solution is cooled to 7–8° C. and purged with nitrogen for about 20 minutes. Thereafter, 0.45 g of azobis(2-amidinopropane) dihydrochloride dissolved in 22.5 g of distilled Water, 1.35 g of sodium peroxodisulfate, dissolved in 25 g of distilled water, and 0.315 g of hydrogen peroxide (35%), dissolved in 22.5 g of distilled water, are added. Subsequently, the polymerization is initiated by adding 0.0675 g of ascorbic acid dissolved in 9 g of water, whereupon a significant rise in temperature occurs. A gel-like product is obtained, the further processing of which will be described in the following Examples.

Example 1b

This Example illustrates the production of another polymer gel having superabsorbent properties.

A solution of 1300 g of acrylic acid, 2015.9 g of distilled water, 6.5 g of polyethylene glycol monoallyl ether acrylate, and 3.9 g of polyethylene glycol diacrylate is prepared. Using 997.10 g of 50% sodium hydroxide solution, partial neutralization (DN=70%) is effected with stirring and cooling. The solution is cooled to 7–8° C. and purged with nitrogen for about 20 minutes. Thereafter, 0.45 g of azobis (2-amidinopropane) dihydrochloride dissolved in 22.5 g of distilled Water, 1.35 g of sodium peroxodisulfate, dissolved in 25 g of distilled water, and 0.315 g of hydrogen peroxide (35%), dissolved in 22.5 g of distilled water, are added. Subsequently, the polymerization is initiated by adding 0.0675 g of ascorbic acid dissolved in 9 g of water, whereupon a significant rise in temperature occurs. A gel-like product is obtained, the further processing of which will be described in the following Examples.

Example 1c

This Example illustrates the production of another polymer gel having superabsorbent properties.

A solution of 1300 g of acrylic acid, 2017.19 g of distilled water, and 3.9 g of triallylamine as crosslinker is prepared. Using 997.10 g of 50% sodium hydroxide solution, partial neutralization (DN=70%) is effected with stirring and cooling. The solution is cooled to 7–8° C. and purged with nitrogen for about 20 minutes. Thereafter, 0.45 g of azobis (2-amidinopropane) dihydrochloride dissolved in 22.5 g of distilled Water, 1.35 g of sodium peroxodisulfate, dissolved in 25 g of distilled water, and 0.315 g of hydrogen peroxide (35%), dissolved in 22.5 g of distilled water, are added. Subsequently, the polymerization is initiated by adding 0.0675 g of ascorbic acid dissolved in 9 g of water, whereupon a significant rise in temperature occurs. A gel-like product is obtained, the further processing of which will be described in the following Examples.

Example 2

500 g of the gels obtained in Example 1a are willowed and sprayed uniformly with a suspension of β-cyclodextrin and Flavith® S108 (Degussa AG, $SiO_2/Al_2O_3$ ratio about 500) in water in amounts as specified in the following Table (given in % dry substance relative to acrylic acid), and subsequently dried to a residual water content of <10% at 150° C. in a circulating air oven.

| Example | Retention [g/g] | β-Cyclodextrin wt.-% | Flavith S108 wt.-% |
| --- | --- | --- | --- |
| 2a | 36.8 | 1 | 0.75 |
| 2b | 36.8 | 2 | 0.75 |
| 2c | 35.5 | 3 | 0.75 |
| 2d | 37.5 | 4 | 0.75 |

Example 3

In this Example, the retention and liquid absorption under pressure of a surface-crosslinked polymer product having superabsorbent properties are examined in the absence of cyclodextrin or cyclodextrin derivatives and zeolite.

50 g of the dried and milled polymer from Examples 1a–c screened to 150–850 μm is wetted with a solution of 0.5 g of ethylene carbonate and 1.5 g of water in a plastic vessel with vigorous stirring and mixed thoroughly using a commercially available household hand mixer (Krups company). Subsequently, the wetted polymer is heated in an oven at a temperature of 180° C. for 30 minutes.

| Example | Retention [g/g] | AAP [g/g] |
|---|---|---|
| 3a | 32.0 | 22.5 |
| 3b | 28.0 | 24.5 |
| 3c | 27.0 | 23.5 |

Example 4

In this Example, surface crosslinking is effected subsequent to adding cyclodextrin and zeolite.

50 g of each dried and milled polymer from Examples 2a–d screened to 150–850 μm is wetted separately with a solution of ethylene carbonate (EC) and water in a plastic vessel with vigorous stirring and mixed thoroughly using a commercially available household hand mixer (Krups company). The solution contains 0.25 g of EC per 1.8 g of water. Subsequently, the wetted polymer is heated in an oven at a temperature of 170° C. for 30 minutes.

| Example | EA(CD) [%] | Retention [g/g] | AAP [g/g] |
|---|---|---|---|
| 4a | 10 | 27.2 | 22.2 |
| 4b | 38 | 26.4 | 21.8 |
| 4c | 56 | 28.6 | 21.5 |
| 4d | 57 | 29.0 | 20.3 |

Comparative Example 3a (Analogous to WO 91/12029)

10 g of methylcellulose (Walocel VP-M 20678) is dispersed with 40 g of Flavith® S108 (Degussa AG, $SiO_2$/$Al_2O_3$ ratio about 500) and 190 g of water using a high speed mixer, subsequently mixed with 50 g of a commercially available superabsorber (Favor® SXM 6860 by the Stockhausen company) in a laboratory mixer, and dried in a fluid-bed dryer at 60° C. in a constant air flow for 20 minutes.

Comparative Example 3b (Analogous to WO 91/12029)

0.25 g of methylcellulose (Walocel VP-M 20678) is dispersed with 1 g of Flavith® S108 and 5 g of water using a high speed mixer, subsequently mixed with 50 g of a commercially available superabsorber (Favor® SXM 6860 by the Stockhausen company) in a laboratory mixer, and dried in a fluid-bed dryer at 60° C. in a constant air flow for 20 minutes.

| Designation | TB [g/g] | AAP 0.3 psi [g/g] | AAP 0.7 psi [g/g] |
|---|---|---|---|
| C3a | 20.5 | 16.2 | 9.0 |
| C3b | 29.0 | 27.5 | 18.4 |
| SXM 6860 | 31.0 | 31.0 | 24.0 |

In addition to a dramatically deteriorated performance, particularly in the absorptive capacity under pressure compared to SXM 6860, the instability of the composite material can already be seen in a heavy formation of dust when mixing or conveying the material.

Comparative Example 4

In this example, cyclodextrin and zeolite are added subsequent to surface crosslinking.

50 g of the product obtained in Example 3 is sprayed with thorough mixing with a suspension of cyclodextrin and zeolite (Flavith® S108, Degussa-Hüls company) in water in the amounts specified in the following Table. The product is dried to a residual water content of <4% in a drying oven.

| Designation | Beta-CD [%] | Flavith S108 [%] |
|---|---|---|
| C4a | 0.5 | 2 |
| C4b | 0.5 | 1 |
| C4c | 2 | 2 |
| C4d | 1 | 1 |

Example 5

The product obtained in Comparative Example 4 is screened, and the fraction having a grain size of 150–850 μm is subjected to a ball mill stability test wherein the product is stressed for 6 minutes at 95 rpm in the ball mill. Likewise, the product obtained in Example 2d is subjected to a ball mill stability test. Again, the products are screened, and the fraction having a grain size of <150 μm is examined for its silicon content using test method 5. As the zeolite that is employed has a grain size markedly below 150 μm, this method allows a determination of the amount of zeolite that has been bound to or incorporated in the polymer having superabsorbent properties. The following quantities of silicon, relative to total dry substance, are found in the samples:

| Product from Example | $SiO_2$ content [%] | Theoretical $SiO_2$ content [%] |
|---|---|---|
| 2d | 0.7 | 0.75 |
| Comp. Ex. C4a | 3.5 | 2 |
| Comp. Ex. C4d | 5.8 | 2 |

Relative to the total amount of polymer of the invention having superabsorbent properties As is clearly recognized, the products of the invention in the fraction of particles <150 μm have significantly less silicon compared to products produced according to prior art, providing evidence that binding of the zeolites to the polymer is significantly stronger in the products according to the invention. When subjecting the material to mechanical stress, large amounts of zeolite are removed from the prior art products, as characterized by the high silicon dioxide content in the fine dust after stressing in the ball mill.

Example 6

This Example examines the reduction in the vapor space concentration of malodorous compounds.

In the measurement of malodorous substances, a polymer with no cyclodextrin and no zeolite is examined as a blank according to test procedure 2, and the vapor space concentration of malodorous substance found is set as 100%. Subsequently, samples containing cyclodextrin and/or zeolite are examined, and the vapor space concentration of malodorous substance is determined. The figures in the right column are calculated as follows: 100×(detected amount of odorous substance from polymer containing CD-zeolite/detected amount of odorous substance from polymer free of CD-zeolite).

Doping With Furfurylmercaptane:

| Polymer from Example | Reduction of furfuryl-mercaptane concentration in the vapor space [%] |
| --- | --- |
| 4a | 62.4 |
| 4b | 63.0 |
| 4c | 71.0 |
| 4d | 75.3 |

The absorbent polymer products of the invention exhibit a significant reduction of malodorous substances.

What is claimed is:

1. An absorbent, crosslinked polymer for water or aqueous body fluids, based on optionally partially neutralized, monoethylenically unsaturated monomers bearing acid groups, wherein the polymer has cyclodextrin or cyclodextrin derivatives and zeolites high in silicon with a silicon oxide/aluminium oxide ratio of >10 at least partially bound covalently, ionically bound thereto or incorporated therein.

2. The polymer according to claim 1, wherein it contains 0.01–50 wt.-% cyclodextrin or cyclodextrin derivatives and at least 0.01–10wt.-% of zeolites high in silicon.

3. The polymer according to claim 2, wherein said polymer has carboxyl groups and the polymer has been coated with 0.01–30 wt % relative to the polymer, of a crosslinker component which reacts with at least two carboxyl groups in the surface layer of the polymer particles, thereby effecting crosslinking.

4. The polymer according to one of claims 1, wherein the extractable amount of cyclodextrin or derivatives thereof is 85% at maximum.

5. A process for producing the polymer according to claim 1, by radical polymerization of an aqueous solution of ethylenically unsaturated, monomers bearing acid groups, crosslinking monomers, and according to the process of solution of suspension polymerization to form a hydrogel, followed by drying, milling/screening, wherein the cyclodextrin component and zeolite high in silicon with a silicon oxide/aluminum oxide ratio of >10 are added to the polymer during a surface cross-linking at the latest.

6. The process for producing polymers according to claim 5, wherein the hydrogel is surface-crosslinked.

7. The process according to claim 5, wherein the pH value of the cyclodextrin solution and/or zeolite suspension is adjusted to >8.

8. Use of the polymer according to claim 1 for improved absorption of odors from body fluids, in constructions for absorbing body fluids, in foamed and non-foamed sheet materials, in packaging materials, in plant breeding, and as soil improver, and as a vehicle and stabilizer for active substances, fertilizers and other active substances being released in a delayed fashion.

9. Use of the polymers according to claim 1 in hygiene articles.

* * * * *

UNITED STATES PATENT AND TRADEMARK OFFICE
CERTIFICATE OF CORRECTION

PATENT NO. : 6,623,848 B2
DATED : September 23, 2003
INVENTOR(S) : Helmut Brehm et al.

It is certified that error appears in the above-identified patent and that said Letters Patent is hereby corrected as shown below:

Title page,
After Item "[65], Prior Publication Data, US 2003/0157318 A1 Aug. 21, 2003" insert -- [30]     Foreign Application Priority Data

August 20, 1999     (DE)     199 39 622.0 --

Column 1,
After the title and before the first paragraph insert

-- This application is a continuation of International Application No. PCT/EP00/07741, internationally filed August 9, 2000. --

Signed and Sealed this

Fourteenth Day of December, 2004

JON W. DUDAS
*Director of the United States Patent and Trademark Office*